United States Patent [19]
Kister et al.

[11] Patent Number: 4,735,704
[45] Date of Patent: Apr. 5, 1988

[54] LIQUID REMOVAL ENHANCEMENT

[75] Inventors: Henry Z. Kister, Monterey Park; James F. Litchfield, South Pasadena, both of Calif.

[73] Assignee: Santa Fe Braun Inc., Alhambra, Calif.

[21] Appl. No.: 864,020

[22] Filed: May 16, 1986

[51] Int. Cl.⁴ .............................................. F23J 3/02
[52] U.S. Cl. ..................................... 208/100; 208/102; 208/340; 208/106; 585/809; 62/121
[58] Field of Search ............... 208/340, 341, 342, 106, 208/100, 103, 105, 102, 130; 585/501, 809; 62/121

[56] References Cited

U.S. PATENT DOCUMENTS

| | | | |
|---|---|---|---|
| 2,973,834 | 3/1961 | Cicalese | 208/340 |
| 3,296,118 | 1/1967 | Czajkowski et al. | 208/102 X |
| 3,342,724 | 9/1967 | Goering | 585/809 |
| 3,375,189 | 3/1968 | Hamblin | 208/100 |
| 3,485,886 | 12/1969 | Mitchell et al. | 585/809 X |
| 3,607,963 | 9/1971 | Danneil et al. | 585/809 X |
| 4,190,520 | 2/1980 | Geuartowski | 208/100 X |
| 4,457,834 | 7/1984 | Caspers et al. | 208/100 X |

FOREIGN PATENT DOCUMENTS 1083464 6/1960 Fed. Rep. of Germany ...... 208/100

OTHER PUBLICATIONS

G. C. Shah, "Troubleshooting Distillation Columns", Chemical Engineering, Jul. 31, 1978, pp. 70-78.

Primary Examiner—Helen M. S. Sneed
Assistant Examiner—Glenn Caldarola
Attorney, Agent, or Firm—Lyon & Lyon

[57] ABSTRACT

An improved process for removing free liquid from a hydrocarbon-rich gas stream is disclosed. Liquid is injected into the gas stream upstream of a chiller and downstream of an acid-gas removal system and any equipment that may affect the water content of the gas stream: compressors, columns, additional knockout drums, heat exchangers or the like. This enhances heat and mass transfer in a manner that both minimizes the formation of small droplets and encourages the coalescence of small droplets in the chiller. As a result, small droplets which would normally pass through a knockout drum and a standard mist eliminator are increased in size, prior to their arrival at a vapor-liquid separator, to larger drops which are easily removed by the vapor-liquid separator, and the mist eliminator.

21 Claims, 1 Drawing Sheet

LIQUID REMOVAL ENHANCEMENT

BACKGROUND OF THE INVENTION

1. Field of the Invention

This invention relates to an improved process for removing free liquid from a chilled hydrocarbon-rich gas stream flowing to a dryer. More particularly, this invention relates to an improved process for removing free liquid, principally water and heavier liquid hydrocarbons having boiling points substantially in excess of that of ethylene, from chilled hydrocarbon-rich gas streams that flow to an ethylene plant primary dryer.

2. DESCRIPTION OF THE PRIOR ART

Drying gaseous hydrocarbon-rich streams is a common operation in hydrocarbon processing plants such as ethylene plants, where a gaseous hydrocarbon mixture is separated into several product and by-product streams at temperatures often as low as $-150°$ F.; in natural gas plants, where heavy components and sometimes inert components such as nitrogen are separated at temperatures sometimes lower than $-200°$ F.; in gas treatment plants, where natural gas must be dried to meet pipeline moisture specifications; and in ammonia plants, where a gaseous hydrocarbon mixture is dried before undergoing low temperature processing.

Drying gaseous hydrocarbon-rich streams is commonly carried out by absorption processes, e.g., gas absorption processes using a hygroscopic solvent such as ethylene glycol, or by adsorption processes in which the water vapor being removed from the gas is adsorbed on the surface of a solid adsorbent or desiccant, such as molecular sieve, alumina, silica gel or the like, which have a high affinity for water and liquids.

In typical absorption systems, dry solvent flowing downwards in an absorber contacts upflowing process gas which contains water vapor. The dry solvent absorbs water from the gas, forming a dry gas stream and a water-rich solvent stream. The water-rich solvent is then passed to a regenerator and heated to remove absorbed water from the solvent. Regenerated solvent, after cooling, is recycled to the absorber.

In a typical adsorption system, water vapor containing process gas flows through a fixed bed of desiccant particles, which keep adsorbing water until the bed surface becomes saturated. When this occurs, the process gas flow is switched to another desiccant bed and the water-saturated dessicant bed is regenerated by flowing dry, heated gas through it to remove adsorbed water.

How well both absorption and adsorption dryers perform depends primarily on the quantity of water contained in the process gas being dried. In the typical adsorption system, an increase in the water content of the process gas stream increases solvent circulation rate, solvent cost and regeneration cost, and can necessitate an increase in equipment size. Similarly, in the typical adsorption system, an increase in the water content of the process gas stream reduces the length of the adsorption cycle and, consequently, increases the frequency of regeneration. This in turn reduces the useful life of the desiccant, and increases the costs of regeneration.

Hydrocarbon process gases can contain water in two forms—as water vapor and as "free water". Free water is water in the liquid state, usually in the form of liquid droplets. Neither form is desirable at the dryer inlet, and both are usually minimized to the greatest practicable extent prior to the process gases' entering a dryer. One way of minimizing water vapor in a hydrocarbon process gas is to cool the gas to as low a temperature as possible short of that at which hydrates are formed. Hydrates are loose solid chemical compounds of hydrocarbons and water which, when formed in processing equipment such as pipelines, heat exchangers and fractionation columns, behave like ice, causing equipment blockages and reducing effective equipment capacity. In most cases, this low temperature will typically be between about 45° F. and about 75° F. As the temperature is lowered, water vapor is condensed from the gas and converted to free water. The process gas containing condensed free water then flows to a vapor-liquid separator, usually a knockout drum equipped with a mist eliminator, in which free water and other condensed liquids in the form of continuous liquid or large drops of liquid (i.e., droplets which are capable of being knocked out by standard mesh pads) are separated from the process gas.

In many instances, the quantity of free water present as fine drops is significant, and there is an incentive to remove these fine drops before drying the gas. Two techniques have been used for this purpose: either a fine mesh pad is installed in the knockout drum, or a filter-coalescer is installed in the process gas line which leads from the knockout drum to the dryer. However, fine mesh pads are sensitive to plugging by any solids or heavy viscous liquids carried over by the process gas. Further, the pressure drop across the mesh pad will increase, sometimes substantially, as plugging progresses. Filter-coalescers, although they can remove finer liquid drops than can fine mesh pads, are also sensitive to plugging and pressure build-up. For this reason, filter-coalescer units are frequently installed in parallel, so that one can be cleaned while the other remains on-line.

Solving the plugging in this fashion, however, introduces others: considerable additional capital expenditures are required, and a significant pressure drop is added to the system. This pressure drop, in turn, increases compressor power requirements and, ultimately, operating costs.

In hydrocarbon processing plants in which neither a fine mesh pad nor a filter-coalescer is installed, there is no significant problem as long as little free water exists in the form of fine droplets in the hydrocarbon-rich gas stream flowing to the dryer. Serious problems are created, however, if appreciable amounts of free water reach the dryer. Absorption cycles and desiccant life can be considerably reduced, thus causing significant increases in operating costs for the purchase of new desiccant and for more frequent regenerations.

Accordingly, there are always incentives to minimize the quantity of water contained in hydrocarbon-rich process gases flowing to a dryer. A low cost method for removing fine liquid droplets from a hydrocarbon-rich process gas stream before the stream reaches the dryer could substantially reduce capital costs in any new plant being built in which such streams are dried, and would also eliminate the problems, with their attendant costs, which arise in new or existing plants whenever free water arrives at the dryer.

Hence, it is an object of this invention to provide an improved process for removing free liquid from a hydrocarbon-rich gas stream flowing to a dryer.

It is also an object of this invention to provide an improved process for removing free liquid, principally water and heavier liquid hydrocarbons having boiling points substantially in excess of that of ethylene, from hydrocarbon-rich gas streams that flow to an ethylene plant primary dryer.

A further object of this invention is to provide an improved process for removing free liquid from a hydrocarbon-rich gas stream flowing through a chiller to a vapor-liquid separator and ultimately to a dryer in which the need to install fine mesh pads or filter-coalescers to remove water before the gas stream reaches the dryer is eliminated.

These and other objects, as well as the nature, scope and utilization of the invention, will become readily apparent to those skilled in the art from the following description, the drawing, and the appended claims.

SUMMARY OF THE INVENTION

The process of this invention accomplishes the removal of free liquid from a hydrocarbon-rich stream flowing to a dryer, without the use of fine mesh pads or filter coalescers, by injecting liquid into the gas stream upstream of the chiller and downstream of any equipment item that may affect the water content of the gas stream, such as compressors, columns, additional knockout drums, heat exchangers or the like.

Operating in this fashion enhances heat and mass transfer in a manner that both minimizes the formation of small droplets and encourages the coalescence of small droplets in the chiller. As a result, small droplets which would normally pass through a knockout drum and a standard mist eliminator are increased in size, prior to their arrival at a vapor-liquid separator, to larger drops which are easily removed by the vapor-liquid separator with a standard mist eliminator.

Liquid drops are formed in a free liquid-containing, hydrocarbon-rich process gas stream fed to a chiller by either or both of two mechanisms:

(1) liquid condensation at the walls, e.g., tube walls, of the chiller, followed by the shearing action of the gas "tearing" liquid droplets away from the surface of the liquid, and (2) condensation of liquid in the bulk of the gas, caused by "cold" being transmitted more rapidly than the vapor flow from the bulk of the gas to the chiller wall.

Both mechanisms, and especially the latter, are likely to cause the formation of small drops when practicing prior art processes. Drop coalescence does take place en route to the liquid-vapor separator, but the amount of coalescence can be relatively small if the size of the droplets and the amount of liquid being condensed in the chiller are small, and if there is little liquid present for liquid interchange between the chilling surfaces, e.g. the surface of chiller tubes, and the gas. Upon arrival at the liquid-vapor separator, most of the small droplets formed initially will still be present as small droplets which the separator and mist eliminator will be unable to remove.

Liquid injection upstream of the chiller, as taught by this invention, enhances the development of larger liquid droplets by providing a sufficient amount of liquid for liquid interchange in the chiller between its chilling surfaces, e.g., the surfaces of chiller tubes, and the gas stream. This interchange will provide, in the form of large drops, surfaces on which vapor can condense, and will enhance the coalescence of the finer droplets. In this interchange, liquid droplets are continuously being transferred from the gas to the liquid on the surfaces of the chiller tubes and from the liquid on the surfaces of the chiller tubes to the gas. The droplets are generated at the liquid surface by the gas shearing or tearing apart the liquid waves flowing along the surfaces of the tubes. Maximum stable droplet size can be estimated using the critical Weber Number for the injected liquid. For example, the critical Weber Number is equal to:

$$(We)_{crit} = 1.5 \times 10^{-3} (\rho V^2) g d/\sigma$$

Where $(\rho V)^2$ is the velocity head of the gas stream, lb/ft sec$^2$, d is the maximum stable droplet diameter, $\mu$m, and $\sigma$ is the surface tension of the liquid, dynes/cm. In a typical ethylene chiller, the critical Weber number and the surface tension of the liquid are both about 30 and the velocity head of the gas is about 2000. Therefore, the maximum stable droplet diameter is about 300 $\mu$m.

This invention approaches the problem of separating free liquid from a hydrocarbon-rich gas stream flowing to a dryer using an entirely different concept than those suggested by the prior art. The aforementioned prior art techniques attempt to solve the problem downstream of the mist eliminator; this invention operates upstream of the mist eliminator. Also, these prior art techniques attempt to remove free water by coalescing it on solid surfaces; this invention controls droplet size distribution to maximize the efficiency of the vapor-liquid separator and mist eliminator system. Finally, the method of this invention is inexpensive and does not introduce the disadvantages of plugging the consequent excessive pressure drops along the path to the dryer inherent in the above-described prior art techniques.

DETAILED DESCRIPTION OF THE INVENTION

Figure 1:
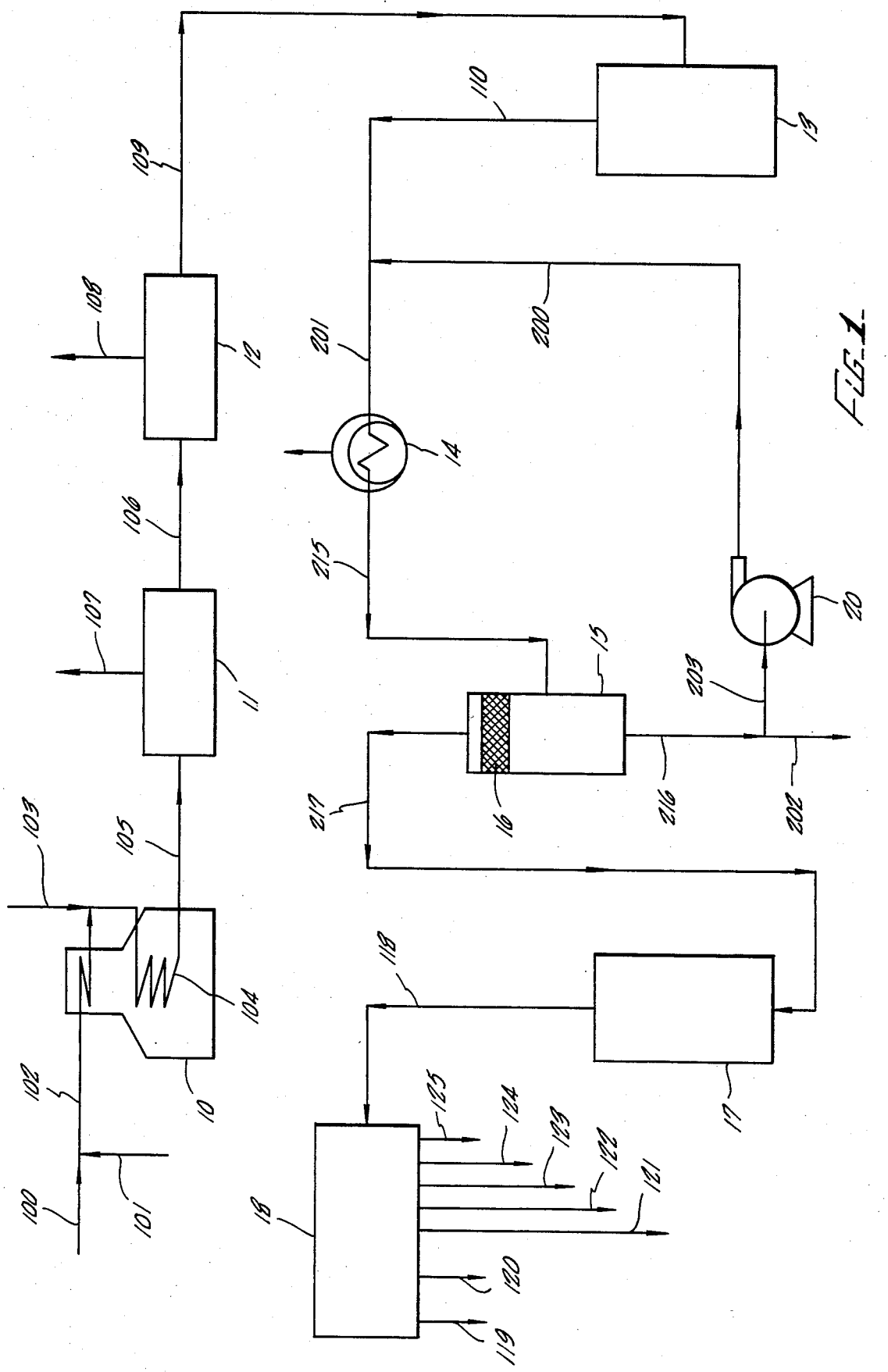
FIG. 1 is a simplified schematic flow diagram of an ethylene plant illustrating a preferred embodiment of the process of this invention.

The ethylene plant illustrated schematically in FIG. 1 can produce 1.0 billion pounds per year of ethylene. However, as would be apparent to one skilled in the art, the present invention is not limited in application to any one particular design of an ethylene plant. Further, although this invention is particularly well-suited for use in ethylene plants, it can also be applied to other plants, such as gas processing and ammonia plants, in which a hydrocarbon-rich stream containing water vapor is chilled, passes through a vapor-liquid separator, and is then dried.

With reference to FIG. 1, a feedstock 100, which may vary considerably as to composition, is fed from a source (not shown) and combined with a vaporized recycle stream 101 containing mainly ethane, propane, or both, being fed from a source (not shown, although the ethane stream 120 which exits the fractionation section 18 of the plant could be used for this purpose) to form a feed stream 102 which is passed into a pyrolysis furnace 10. An ethylene plant generally has several pyrolysis furnaces operating in parallel. To ensure favorable cracking conditions and avoid excessive coking in the furnace tubes, stream 103 from a source (not shown) is injected into the feed stream 102 to form a hydrocarbon-steam mixture 104 whose hydrocarbon components are cracked in the pyrolysis furnace 10 to form a cracked hydrocarbon-steam mixture 105. This mixture is then cooled by passing it to a cooling system 11.

A gaseous wet hydrocarbon stream 106 and a condensate stream 107 exit the cooling system 11. The condensate stream 107 contains most of the condensed steam injected into the furnace 10 and some of the heavy hydrocarbons, and is removed from the system. The gaseous wet hydrocarbon stream is saturated with water vapor and with heavy hydrocarbons, and flows to the suction side of the low stages of a cracked gas compressor system 12, which compresses the wet gas stream by a succession of compression steps, each compression step being followed by a cooling step and a vapor-liquid separation step.

The vapor-liquid separation steps are necessary because as the pressure of the compressed gas increases, the amounts of water and heavier hydrocarbons that saturate the gas decrease, and the water and heavier hydrocarbons present in excess of the saturation quantity are condensed and removed from the system. The low stages of the cracked gas compressor thus generate a wet gas stream saturated with water vapor and heavier hydrocarbons 109, which exits the cracked gas compressor system 12, and a condensed liquid stream 108 which is removed from the system.

The wet gas stream 109 is typically at a pressure ranging from 85 to 550 psia, and a temperature between 70° and 150° F., and flows from the compressor system 12 to an acid-gas removal system 13, which absorbs acid-gas impurities such as hydrogen sulfide and carbon dioxide by contact first with an aqueous amine solution and then with an aqueous caustic solution to form a wet acid-gas free gas stream 110 which leaves the acid-gas removal system 13. In many plants, only an aqueous caustic solution is used to remove the acid-gas. The wet acid-gas free gas stream 110 leaving the acid gas removal system 13 is at a pressure ranging from 80 to 545 psia and a temperature between 70° and 150° F., is saturated with water vapor, and is close to saturation with heavier hydrocarbons.

This wet acid-gas free gas stream 110 is combined with a liquid injection stream 200 to form a gas/liquid stream 201. The liquid injection stream 200 can be a recycle stream pumped from a vapor-liquid separator 15 by a pump 20, or it can be a liquid stream that originates elsewhere, and thus can be water, a hydrocarbon-and-water mixture, a hydrocarbon liquid, or the like.

Liquid injection upstream of the chiller 14 can be carried out by either a device specifically designed for spreading liquid into a gas stream, such as a spray nozzle, or by merely introducing a stream of liquid into the pipeline and relying on gas turbulence and kinetic energy in the downstream conduit and exchanges to break up the liquid and disperse it. The quantity of liquid used is that amount of liquid needed to ensure that a sufficient amount of liquid is dispersed at the inlet to each of the chiller tubes in the chiller 14 to provide a sufficient amount of liquid in the gas stream for liquid interchange between the chilling surfaces of the chiller 14 and the liquid-injected gas stream. To minimize the quantity of fresh liquid injected into the system, liquid collected by the vapor-liquid separator 15 can be recycled and used as the injection liquid. Ordinarily, this amount will range from about 0.5 to about 10 lb/hr of liquid per circumferential inches of chiller tubing, and preferably closer to about 1.0 to minimize the additional energy needed to recycle the liquid and pass the liquid through the chiller system.

Following the introduction of the liquid injection stream 200, the gas/liquid stream 201 then flows into a chiller 14, where it is chilled by heat exchange with a refrigerant stream to form a chilled stream 215 which leaves the chiller at a temperature ranging from 40° F. to 60° F. The chiller 14 may be a single heat exchanger or a plurality of heat exchangers. The chilled stream 215 exiting the chiller 14 consists of wet vapor, saturated with water and heavier hydrocarbons at the chilled temperature and pressure, as well as the condensed and injected hydrocarbon-and-water liquid, which is present largely in the form of large drops. The chilled stream 215 flows to a vapor-liquid separator 15 which is equipped with a mist eliminator 16. The vapor-liquid separator 15 separates the chilled stream 215 into a chilled liquid stream 216 and a chilled gas stream 217. The chilled liquid stream 216 is split into a liquid recycle stream 203 and a liquid drawoff stream 202. This liquid drawoff stream 202 is removed from the system. The liquid recycle stream 203 is pumped by a pump 20 to become the liquid injection stream 200 to be injected upstream of the chiller 14. When the liquid injection stream is not a recycle stream but originates elsewhere, the liquid stream 203 and the pump 20 can be eliminated. The chilled gas stream 217 is saturated with water and heavier hydrocarbons, but contains little or no free water.

The chilled gas stream 217 flows into a dryer 17, which removes water vapor contained in the chilled gas stream to form a dry gas stream 118 which exits the dryer 17. Usually, the dryer 17 contains molecular sieve, alumina or silica gel desiccants, and removes water vapor by adsorption, but a gas absorption dryer or dryers may also be used. To ensure continuous operation when adsorbent dryers are used, two or more dryers 17 are installed in parallel to enable regeneration of desiccant which has become saturated with water. A typical desiccant adsorption cycle is 1–3 days for molecular sieve desiccants, and typical desiccant life is 5–10 years. Dessicant regeneration is usually accomplished by taking the water-saturated desiccant dryer 17 off line and passing hot gas through it.

The dry gas stream 118 leaving the dryer flows to the high compression stages of a cracked gas compressor and fractionation section 18 of the plant. In many plants, the low compression stages of their cracked gas compressors compress the gas to a sufficiently high pressure, and no high compression stages are required. In other plants, the high compression stages are integrated within the fractionation sections. In the fractionation section the dry gas stream 118 is separated into a plurality of product and byproduct streams which always include an ethylene product stream 119, an ethane stream 120 which is generally recycled as feedstock to the furnaces, and a variety of other product and by-product streams e.g., 121–125.

In order that those skilled in the art can more fully understand this invention, the following example is set forth. This example is given solely for purposes of illustration, and should not be considered as expressing limitations unless so set forth in the appended claims.

EXAMPLE I

In this examaple an ethylene plant design using conventional technology is compared to a design using this invention. Each of these designs represents a plant producing 1 billion lb/yr ethylene from ethane feedstock. Table 1 defines the process conditions along the route from the acid-gas removal system 13 to the dryer 17 (see FIG. 1) in the plant using conventional technology. In this case the wet acid-gas free gas stream 110 leaving the acid-gas removal system is at a pressure of 200 psia and a temperature of 100° F. This stream is fed directly (i.e., with no injection of a liquid injection stream 200 to a chiller 14, where the stream is chilled by heat exchange with a refrigerant stream to form a chilled stream 215 exiting the chiller 14 at a temperature of 55° F. and a pressure of 195 psia. The chilled stream 215 consists of wet vapor, saturated with water and heavier hydrocarbons, at a temperature of 55° F. and a pressure of 195 psia, as well as condensed hydrocarbon-and-water liquid, which is present largely in the form of water drops. The chilled stream 215 flows to a vapor-liquid separator 15 which is equipped with a mist eliminator 16. The chilled stream is separated into a chilled liquid stream 216 which is removed from the system and a chilled gas stream 217 which also contains the liquid droplets not removed by the vapor-liquid separator 15 or the mist eliminator 16, which flows into the dryer 17.

flows into a chiller 14, where it is chilled by heat exchange with a refrigerant stream to form a chilled stream 215 which leaves the chiller 14 at a pressure of 195 psia and a temperature of 55° F. This chilled stream 215 consists of wet gas, saturated with water and heavier hydrocarbons at a temperature of 55° F. and a pressure of 195 psia, as well as the condensed and injected hydrocarbon-and-water liquid, which is present largely in the form of large drops. The chilled stream 215 flows to a vapor-liquid separator 15, which is equipped with a mist eliminator 16, where the chilled stream is separated into a chilled liquid stream 216 and a chilled gas stream 217. The chilled liquid stream 216 is split into a liquid recycle stream 203 and a liquid drawoff 202. The liquid drawoff stream 202 is removed from the system, while the liquid recycle stream is pumped by a pump 20 to become the liquid injection stream 200 and is injected upstream of the chiller 14. The chilled gas stream 217 is saturated with water and heavier hydrocarbons, but contains little or no free water.

The process carried out using this invention reduces the water content of the chilled gas stream entering the

TABLE I

| STREAM NO. DESCRIPTION | 110 (WET, ACID-GAS FREE GAS STREAM) | 215 (CHILLED STREAM) | 216 (CHILLED LIQUID STREAM) | 217 (CHILLED GAS STREAM) |
| --- | --- | --- | --- | --- |
| STREAM COMPOSITION, MOL % (WATER-FREE BASIS) | | | | |
| $N_2$ | 0.5 | 0.5 | — | 0.5 |
| CO | 0.4 | 0.4 | — | 0.4 |
| $H_2$ | 31.0 | 31.0 | — | 31.0 |
| $CH_4$ | 13.2 | 13.2 | 0.9 | 13.2 |
| $C_2$ | 51.0 | 51.0 | 9.3 | 51.1 |
| $C_3$ | 2.6 | 2.6 | 1.9 | 2.6 |
| $C_4$ | 0.7 | 0.7 | 1.9 | 0.7 |
| $C_5+$ | 0.6 | 0.6 | 86.1 | 0.5 |
| FLOW RATE, LB/HOUR, TOTAL | 295,800 | 295,800 | 1600 | 294,200 |
| TEMP, °F. | 100 | 55 | 55 | 55 |
| PRESSURE, PSIA | 200 | 195 | 195 | 195 |
| WATER, LB/HOUR, TOTAL | 1250 | 1250 | 650 | 600 |
| FREE WATER, LB/HOUR | — | 950 | 650 | 300 |

Table 2 defines the process conditions along the route from the acid gas removal system 13 to the dryer 17 using this invention. In this case the wet acid-gas free stream 100 leaves the acid-gas removal system at a pressure of 200 psia and a temperature of 100° F., and is combined with a liquid injection stream 200 at a temperature of 55° F. to form a gas/liquid stream which then dryer by about 50 percent, due to the elimination of free water, as can be seen by comparing the results set out in Table 1 with those of Table 2.

TABLE 2

| STREAM NO. DESCRIPTION | 110 (WET ACID-GAS FREE GAS STREAM | 200 (LIQUID INJECTION STREAM | 203 (LIQUID RECYCLE STREAM | 215 (CHILLED STREAM | 216 (CHILLED LIQUID STREAM | 202 (CHILLED DRAWOFF STREAM | 217 (CHILLED GAS STREAM |
| --- | --- | --- | --- | --- | --- | --- | --- |
| STREAM COMPOSITION, MOL % (WATER-FREE BASIS) | | | | | | | |
| $N_2$ | 0.5 | — | — | 0.5 | — | — | 0.5 |
| CO | 0.4 | — | — | 0.4 | — | — | 0.4 |
| $H_2$ | 31.0 | — | — | 31.0 | — | — | 31.0 |
| $CH_4$ | 13.2 | 0.9 | 0.9 | 13.2 | 0.9 | 0.9 | 13.2 |
| $C_2$ | 51.0 | 9.3 | 9.3 | 51.0 | 9.3 | 9.3 | 51.1 |
| $C_3$ | 2.6 | 1.9 | 1.9 | 2.6 | 1.9 | 1.9 | 2.6 |
| $C_4$ | 0.7 | 1.9 | 1.9 | 0.7 | 1.9 | 1.9 | 0.7 |
| $C_5+$ | 0.6 | 86.1 | 86.1 | 0.6 | 86.1 | 86.1 | 0.5 |
| FLOW RATE, LB/HOUR, | 295,800 | 3,000 | 3,000 | 298,800 | 4,900 | 1,900 | 293,900 |
| TEMP, °F. | 100 | 55 | 55 | 55 | 55 | 55 | 55 |
| PRESSURE, PSIA | 200 | 230 | 195 | 195 | 195 | 195 | 195 |
| WATER, LB/HOUR, TOTAL | 1250 | 1,500 | 1,500 | 2,750 | 2,450 | 950 | 300 |
| FREE WATER, LB/HOUR | — | 1,500 | 1,500 | 2,450 | 2,450 | 950 | — |

Thus, liquid injection upstream of the chiller will enhance the formation of large liquid droplets by:

(1) substantially increasing the amount of liquid surface on which vapor can condense in the bulk of the gas, thus suppressing the formation of small drops;

(2) enhancing the heat and mass transfer exchange of the liquid between the gas and chilling surfaces (e.g. the walls of the chiller tubes), thereby converting small drops to larger ones, and (3) providing liquid drop surface for coalescing fine drops into larger drops.

Further, this invention can be incorporated into new or existing plants at comparatively little cost, since to convert a process using conventional technology into one which takes advantage of this invention, one need only add an injection line and possibly a pump (and, if desired, a spray device for spreading the injected liquid into the gas stream) to the conventional design. In doing so, the only added operating cost is the cost of running the pump, which is low.

The above discussion of this invention is directed primarily to preferred embodiments and practices thereof. Further modifications are also possible without departing from the inventive concept. Thus, for example, any hydrocarbon-rich stream containing water vapor from which substantially all or at least a preponderant amount of the water is to be separated can be treated in accordance with this invention before the stream is passed to a chiller. Accordingly, it will be readily apparent to those skilled in the art that still further changes and modifications in the actual implementation of the concepts described herein can readily be made without departing from the spirit and scope of the invention as defined by the following claims.

We claim:

1. In a process for removing free liquid from a hydrocarbon-rich gas stream containing water flowing to a chiller, then to a vapor-liquid separator, and then to a dryer, the improvement comprising the steps of:
   injecting liquid into the gas stream upstream of a chiller to form a liquid-injected gas stream;
   passing the liquid-injected gas stream to a chiller and condensing heavier hydrocarbon components and water therefrom in the chiller to form a chilled gas-liquid mixture;
   separating the chilled gas-liquid mixture in a vapor-liquid separator into a chilled liquid stream and a chilled gas stream; and
   utilizing the chilled gas stream as a dryer feed stream.

2. A process as recited in claim 1 wherein the hydrocarbon-rich gas stream is saturated with heavier hydrocarbons and water.

3. A process as recited in claim 1 wherein the liquid injected upstream of the chiller is recycled from the vapor-liquid separator.

4. A process as recited in claim 1 wherein the liquid injected upstream of the chiller is passed from a source located elsewhere in the plant or in a different plant.

5. A process as recited in claim 1 wherein the hydrocarbon-rich gas stream flows from an aqueous acid-gas removal system to the point upstream of the chiller at which the liquid is injected.

6. A process as recited in claim 1 wherein the dryer uses an absorption process to remove water.

7. A process as recited in claim 1 wherein the dryer uses an adsorption process to remove water.

8. A process as recited in claim 1 wherein the vapor-liquid separator contains a mist eliminator.

9. A process for removing free liquid from a hydrocarbon-rich gas stream comprising the steps of:
   injecting liquid into the gas stream to form a liquid-injected gas stream;
   chilling the liquid-injected gas stream in a chiller to form a chilled gas-liquid stream containing condensed water;
   separating the chilled gas-liquid mixture in a vapor-liquid separator into a chilled liquid stream and a chilled gas stream;
   utilizing the chilled gas stream as a feed to a dryer.

10. A process as recited in claim 9 wherein the vapor-liquid separator contains a mist eliminator.

11. A process as recited in claim 9 wherein the hydrocarbon-rich gas stream flows from an aqueous acid-gas removal system to the point upstream of the chiller at which the liquid is injected.

12. In an improved process for producing ethylene wherein a feed stream is cracked in a pyrolysis furnace and treated to form a hydrocarbon-rich, acid-gas free, water vapor-saturated stream which is then treated to remove water, then passed to a dryer and then to another treatment process to form a plurality of product and byproduct streams, the improvement comprising the steps of:
   injecting liquid into the hydrocarbon-rich, water vapor saturated gas stream past the point at which acid-gas is removed and upstream of a chiller to form a liquid-injected gas stream;
   chilling the liquid-injected gas stream in a refrigerated chiller to form a chilled gas-liquid mixture;
   separating the chilled gas-liquid mixture in a vapor-liquid separator into a chilled liquid stream and a chilled gas stream;
   utilizing the chilled gas stream as a dryer feed stream.

13. A process as recited in claim 12 where the dryer contains molcular sieve desiccant.

14. A process as recited in claim 12, where the vapor-liquid separator contains a mist eliminator.

15. A process as recited in claim 12 where the acid-gas removal unit utilizes caustic or amine solution.

16. A process as recited in claim 12 wherein the liquid injected upstream of the chiller is recycled from the vapor-liquid separator.

17. A process as recited in claim 12 wherein the liquid injected upstream of the chiller is passed from a source located elsewhere in the plant or outside the plant.

18. A process for producing ethylene by pyrolysis in an olefins plant comprising the steps of:
   passing a feed stream to a pyrolysis furnace;
   cracking the feed stream in the pyrolysis furnace to form a cracked gas stream;
   treating the cracked gas stream to generate a compressed hydrocarbon-rich cracked gas stream, free of acid-gases and saturated with water vapor;
   removing liquid by:
   (1) injecting liquid into the compressed gas stream to form a liquid-injected gas stream;
   (2) passing the liquid-injected gas stream into a chiller to form a chilled gas-liquid stream;
   (3) passing the chilled gas-liquid stream into a vapor-liquid separator to form a chilled liquid stream and a chilled gas stream;
   (4) utilizing the chilled gas stream as a feed stream to a dryer to form a dry, chilled gas stream; and
   treating the dry, chilled gas stream to separate it into product and byproduct streams.

19. The process as recited in claims 1, 9, 12 or 18 wherein said liquid injected into the gas stream provides sufficient liquid in the gas stream for liquid interchange between the chilling surface of the chiller and the gas stream.

20. A process as recited in claims 1, 9, 12 or 18 wherein the liquid is injected into the gas stream at a rate to achieve a total liquid rate of from about 0.05 to 10 lb/hr of liquid per circumferential inches of chiller tubing.

21. A process for removing water from a hydrocarbon gas stream containing free liquid water comprising the steps of:
   injecting liquid water into the gas stream upstream of a chiller to form a liquid water-gas stream;
   chilling the gas stream in a refrigerated chiller to form a chilled liquid water-gas mixture;
   separating the chilled liquid water-gas mixture into a chilled liquid water stream and a chilled gas stream; and
   utilizng the chilled gas stream as a dryer feed stream.

* * * * *